(12) United States Patent
Yang et al.

(10) Patent No.: US 12,008,073 B2
(45) Date of Patent: *Jun. 11, 2024

(54) MYOCARDIUM IMAGE ANALYSIS METHOD AND DEVICE

(71) Applicants: THE ASAN FOUNDATION, Seoul (KR); UNIVERSITY OF ULSAN FOUNDATION FOR INDUSTRY COOPERATION, Ulsan (KR)

(72) Inventors: Dong Hyun Yang, Seoul (KR); June Goo Lee, Seoul (KR); Young-Hak Kim, Seoul (KR)

(73) Assignees: THE ASAN FOUNDATION, Seoul (KR); UNIVERSITY OF ULSAN FOUNDATION FOR INDUSTRY COOPERATION, Ulsan (KR)

( * ) Notice: Subject to any disclaimer, the term of this patent is extended or adjusted under 35 U.S.C. 154(b) by 498 days.

This patent is subject to a terminal disclaimer.

(21) Appl. No.: 17/293,638

(22) PCT Filed: Nov. 7, 2019

(86) PCT No.: PCT/KR2019/015059
§ 371 (c)(1),
(2) Date: May 13, 2021

(87) PCT Pub. No.: WO2020/101265
PCT Pub. Date: May 22, 2020

(65) Prior Publication Data
US 2022/0012532 A1 Jan. 13, 2022

(30) Foreign Application Priority Data
Nov. 14, 2018 (KR) .................. 10-2018-0140025

(51) Int. Cl.
*G06F 18/214* (2023.01)
*A61B 6/00* (2006.01)
(Continued)

(52) U.S. Cl.
CPC ........ *G06F 18/214* (2023.01); *G06F 18/2163* (2023.01); *G06N 3/04* (2013.01);
(Continued)

(58) Field of Classification Search
CPC ..... G06F 18/214; G06F 18/2163; G06N 3/04; A61B 6/032; A61B 6/5217; A61B 6/481;
(Continued)

(56) References Cited

U.S. PATENT DOCUMENTS 9,924,869 B2   3/2018   Kim et al.
9,990,729 B2   6/2018   Kang et al.
(Continued)

FOREIGN PATENT DOCUMENTS

JP          5641792 B2      12/2014
KR    10-2014-0015984 A     2/2014
(Continued)

OTHER PUBLICATIONS

International Search Report dated Feb. 12, 2020 in PCT/KR2019/015059 filed on Nov. 7, 2019, 2 pages.

*Primary Examiner* — Lewis G West
(74) *Attorney, Agent, or Firm* — Oblon, McClelland, Maier & Neustadt, L.L.P.

(57) ABSTRACT

A myocardium image analysis method comprising acquiring a target image including precontrast-enhanced myocardium, based on a type of coronary artery related to the myocardium, distinguishing the myocardium included in the target image, using an artificial neural network, providing information on the distinguished myocardium, wherein the artificial neural network is trained based on a training database
(Continued)

generated by matching images for training of precontrast-enhanced coronary artery and myocardium and images for training of postcontrast-enhanced coronary artery and myocardium.

13 Claims, 4 Drawing Sheets

(51) Int. Cl.
*A61B 6/03* (2006.01)
*G06F 18/21* (2023.01)
*G06N 3/04* (2023.01)

(52) U.S. Cl.
CPC .............. *A61B 6/032* (2013.01); *A61B 6/5217* (2013.01); *G06V 2201/03* (2022.01)

(58) Field of Classification Search
CPC ........... A61B 6/504; A61B 6/503; A61B 6/48; A61B 6/54; G06V 2201/03; G16H 30/40; G16H 50/20
See application file for complete search history.

(56) References Cited

U.S. PATENT DOCUMENTS

| | | | |
|---|---|---|---|
| 11,633,146 B2* | 4/2023 | Leng | A61B 5/004 600/423 |
| 11,730,437 B2* | 8/2023 | Min | A61B 6/463 382/131 |
| 2010/0198054 A1* | 8/2010 | Ewing | A61B 5/7267 600/420 |
| 2013/0072790 A1* | 3/2013 | Ludwig | G06F 17/00 703/11 |
| 2014/0029835 A1* | 1/2014 | Kim | A61B 5/0044 382/134 |
| 2016/0155234 A1* | 6/2016 | Kang | A61B 6/032 345/419 |
| 2016/0300343 A1* | 10/2016 | Gazit | G16H 50/50 |
| 2016/0300351 A1* | 10/2016 | Gazit | G06T 7/187 |
| 2018/0055469 A1 | 3/2018 | Nam et al. | |
| 2018/0276817 A1* | 9/2018 | Isgum | G06T 7/10 |
| 2019/0188852 A1* | 6/2019 | Reicher | G06T 7/0014 |

FOREIGN PATENT DOCUMENTS

| | | |
|---|---|---|
| KR | 10-2016-0064562 A | 6/2016 |
| KR | 10-2016-0103482 A | 9/2016 |
| KR | 10-1703564 B1 | 2/2017 |

* cited by examiner

MYOCARDIUM IMAGE ANALYSIS METHOD AND DEVICE

BACKGROUND OF THE DISCLOSURE

Field of the Disclosure

The present disclosure relates to a device and a method for analyzing an image of myocardium by using an artificial neural network.

Related Art

A coronary artery is an artery that surrounds the heart and supplies oxygen and nutrition to myocardium which is the muscle of the heart. The heart performs a function by continuously supplying the oxygen and the nutrition to the myocardium from the coronary artery. If a disease occurs in the coronary artery and the oxygen and the nutrition are not supplied to the myocardium, a person may die due to occurrence of a cardiovascular disease such as myocardial infarction.

The coronary artery is located in a form to surround the heart with a coronary. Accordingly, the coronary arteries can be classified to detailed types based on the location of the coronary artery on the heart. For example, the type of coronary artery may include a left coronary artery (LCA), a left main coronary artery (LMCA), a left anterior descending coronary artery (LAD), a proximal left anterior descending artery, a middle left anterior descending artery, a distal left anterior descending artery, a right coronary artery (RCA), a proximal right coronary artery, a middle right coronary artery, a distal right coronary artery, and a posterior descending artery (PDA).

As such, by the form in which the coronary artery is located, the coronary artery supplies the oxygen and the nutrition to the myocardium positioned adjacent thereto. As a result, when the disease occurs at a part of the coronary artery, in which region of the coronary artery the disease occurs may be determined and furthermore, treatment may be more precisely performed by identifying a region of the myocardium relating to the region of the coronary artery in which the disease occurs or a cardiovascular disease may be diagnosed.

However, despite an effect on the division of the area of the myocardium, there is a problem that accuracy or objectivity is somewhat low, since distinguishing of the region of the myocardium related to each coronary artery should rely on the experience of a doctor or an analyst up to now.

Patent Document

Korean Patent Registration No. 10-1865275 (Registered on May 31, 2018)

SUMMARY

A problem to be solved by the present disclosure is to provide a device and a method for analyzing a region of myocardium related according to a type of coronary artery in a myocardium image by using an artificial neural network.

However, the problem to be solved by the present disclosure is not limited to the problem mentioned above, and is not mentioned, but includes an object that can be clearly understood by those skilled in the art to which the present disclosure pertains from the following description.

In accordance with one embodiment of the present disclosure, there is provided a myocardium image analysis method comprising: acquiring a target image including precontrast-enhanced myocardium; based on a type of coronary artery related to the myocardium, dividing up the myocardium included in the target image, using an artificial neural network; and providing information on the distinguished myocardium, wherein the artificial neural network is trained based on a training database generated by matching images for training of precontrast-enhanced coronary artery and myocardium and pre-acquired images for training of postcontrast-enhanced coronary artery and myocardium.

Further, the type of coronary arteries includes a left coronary artery (LCA), a left main coronary artery (LMCA), a left anterior descending coronary artery (LAD), a proximal left anterior descending artery, a middle left anterior descending artery, a distal left anterior descending artery, a right coronary artery (RCA), a proximal right coronary artery, a middle right coronary artery, a distal right coronary artery, and a posterior descending artery (PDA).

Further, the dividing up of the myocardium includes dividing up the myocardium according to the type of coronary artery which is adjacent to the myocardium and exerts an influence on the myocardium.

Further, the training database includes information on at least one of a size, a location, a shape, and a length of a region of the myocardium related for each type of the coronary artery, the artificial neural network includes a fully convolutional network (FCN), and the region of the myocardium includes a myocardium region connected to the left coronary artery, a myocardium region connected to the left main coronary artery, a myocardium region connected to the left anterior descending coronary artery, a myocardium region connected to the proximal left anterior descending artery, a myocardium region connected to the middle left anterior descending artery, a myocardium region connected to the distal left anterior descending artery, a myocardium region connected to the right coronary artery, a myocardium region connected to the proximal right coronary artery, a myocardium region connected to the middle right coronary artery, a myocardium region connected to the distal right coronary artery, and a myocardium region connected to the posterior descending artery.

Further, images for training of the precontrast-enhanced coronary artery and myocardium and the images for training of the postcontrast-enhanced coronary artery and myocardium are images on the same target.

Further, the target image may a computed tomography (CT) image.

In accordance with one embodiment of the present disclosure, there is provided a myocardium image analysis device comprising: a target image acquisition unit acquiring a target image including precontrast-enhanced myocardium; based on a type of coronary artery related to the myocardium, a myocardium distinguishing unit dividing up the myocardium included in the target image, using an artificial neural network; and providing information on the distinguished myocardium, wherein the artificial neural network is trained based on a training database generated by matching images for training of precontrast-enhanced coronary artery and myocardium and images for training of postcontrast-enhanced coronary artery and myocardium.

Further, the type of coronary arteries includes a left coronary artery (LCA), a left main coronary artery (LMCA), a left anterior descending coronary artery (LAD), a proximal left anterior descending artery, a middle left anterior descending artery, a distal left anterior descending artery, a right coronary artery (RCA), a proximal right coronary artery, a middle right coronary artery, a distal right coronary artery, and a posterior descending artery (PDA).

Further, the myocardium distinguishing unit divides the myocardium according to the type of coronary artery which may adjacent to the myocardium and exerts an influence on the myocardium.

Further, the training database may include information on at least one of a size, a location, a shape, and a length of a region of the myocardium related for each type of the coronary artery, the artificial neural network includes a fully convolutional network (FCN), and the distinguished region of the myocardium includes a myocardium region connected to the left coronary artery, a myocardium region connected to the left main coronary artery, a myocardium region connected to the left anterior descending coronary artery, a myocardium region connected to the proximal left anterior descending artery, a myocardium region connected to the middle left anterior descending artery, a myocardium region connected to the distal left anterior descending artery, a myocardium region connected to the right coronary artery, a myocardium region connected to the proximal right coronary artery, a myocardium region connected to the middle right coronary artery, a myocardium region connected to the distal right coronary artery, and a myocardium region connected to the posterior descending artery.

Further, the images for training of the precontrast-enhanced coronary artery and myocardium and the images for training of the postcontrast-enhanced coronary artery and myocardium are images for the same target.

Further, the target image may a computed tomography (CT) image.

In accordance with one embodiment of the present disclosure, there is provided a computer readable recording medium storing a computer program, comprising: acquiring a target image including precontrast-enhanced myocardium; based on a type of coronary artery related to the myocardium, dividing up the myocardium included in the target image, using an artificial neural network; and providing information on the distinguished myocardium, wherein the artificial neural network includes a command for allowing a processor to perform a myocardium image analysis method in which training is performed based on a training database generated by matching images for training of precontrast-enhanced coronary artery and myocardium and images for training of postcontrast-enhanced coronary artery and myocardium.

A device and a method for analyzing a myocardium according to an embodiment of the present disclosure can provide information on myocardium having accuracy, reliability, and objectivity by distinguishing a region of the myocardium in a myocardium image to regions related for each coronary artery by using an artificial neural network.

Meanwhile, effects which can be obtained in the present disclosure are not limited to the aforementioned effects and other unmentioned effects will be clearly understood by those skilled in the art to which the present disclosure pertains from the following description.

DESCRIPTION OF EXEMPLARY EMBODIMENTS

The advantages and features of the present disclosure and the methods of accomplishing these will be clearly understood from the following description taken in conjunction with the accompanying drawings. However, embodiments are not limited to those embodiments described, as embodiments may be implemented in various forms. It should be noted that the present embodiments are provided to make a full disclosure and also to allow those skilled in the art to know the full range of the embodiments. Therefore, the embodiments are to be defined only by the scope of the appended claims.

In describing the embodiments of the present disclosure, if it is determined that detailed description of related known components or functions unnecessarily obscures the gist of the present disclosure, the detailed description thereof will be omitted. Further, the terminologies to be described below are defined in consideration of functions of the embodiments of the present disclosure and may vary depending on a user's or an operator's intention or practice. Accordingly, the definition thereof may be made on a basis of the content throughout the specification.

The present disclosure may be modified and include various embodiments. Specific embodiments will be exemplarily illustrated in the drawings and described in the detailed description of the embodiments. However, it should be understood that they are not intended to limit the present disclosure to specific embodiments but rather to cover all modifications, similarities, and alternatives that are included in the spirit and scope of the present disclosure.

The terms used herein, including ordinal numbers such as "first" and "second" may be used to describe, and not to limit, various components. The terms simply distinguish the components from one another.

When it is said that a component is "connected" or "linked" to another component, it should be understood that the former component may be directly connected or linked to the latter component or a third component may be interposed between the two components.

Figure 1:
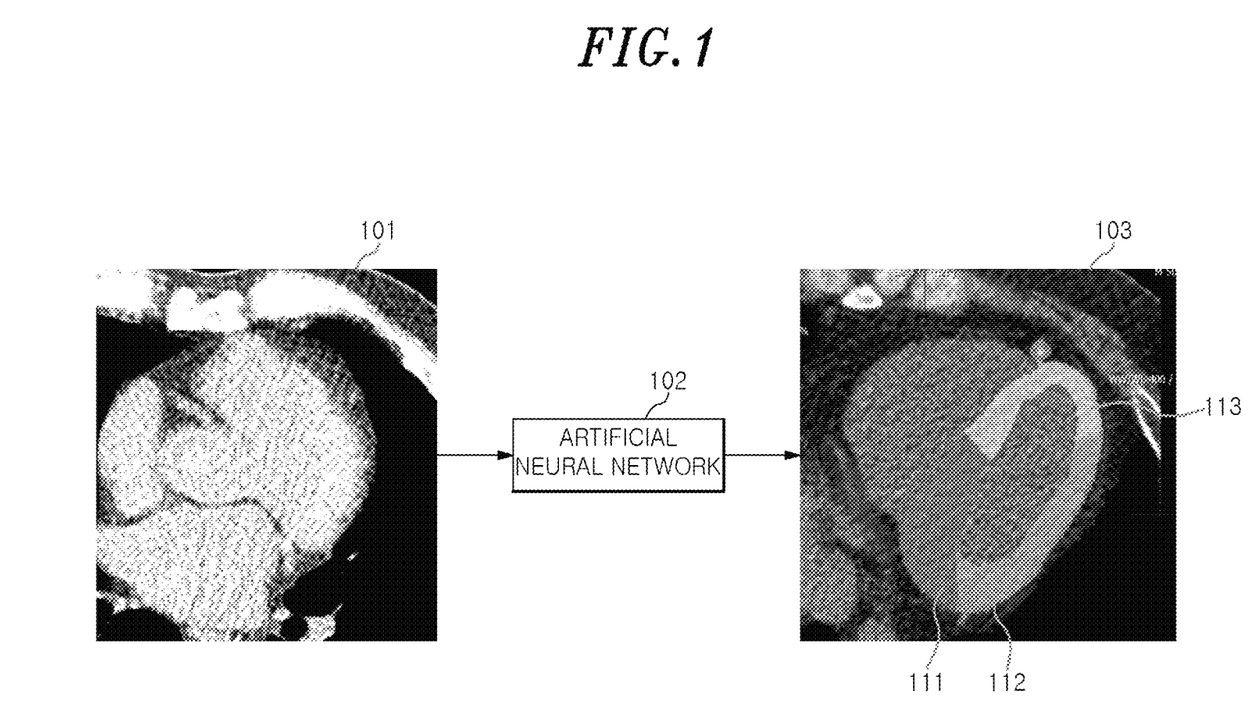
FIG. 1 conceptually illustrates a myocardium image analysis method using an artificial neural network according to an embodiment of the present disclosure.

FIG. 1 conceptually illustrates a myocardium image analysis method using an artificial neural network according to an embodiment of the present disclosure.

Referring to FIG. 1, an input image 101 may be an image (hereinafter, referred to as 'myocardium image') of a heart region including myocardium. More specifically, the input image 101 may include a precontrast-enhanced myocardium image. The precontrast-enhanced myocardium image may be an image in which distinguishing of each organ included in the image is ambiguous.

The region of the myocardium included in the input image 101 may be identified by an artificial neural network 102. For example, as illustrated in FIG. 1, the identified myocardium region may be emphasized to be distinguished from other parts and provided as an output image 103.

Emphasized parts 111, 112, and 113 of the output image 103 illustrated in FIG. 1 may be round band-shaped myocardium, and the myocardium region of the output image 103 may be distinguished and displayed from regions for other organs. Meanwhile, the myocardium region may be divided in detail according to the type of coronary artery associated therewith. As a result, the myocardium region of the output image 103 may be divided into a first myocardium region 111, a second myocardium region 112, and a third myocardium region 113. Here, each myocardium region may be a region to which oxygen and nutrition are supplied by different coronary arteries.

Meanwhile, the coronary arteries may be classified to a left coronary artery (LCA), a left main coronary artery (LMCA), a left anterior descending coronary artery (LAD), a proximal left anterior descending artery, a middle left anterior descending artery, a distal left anterior descending artery, a right coronary artery (RCA), a proximal right coronary artery, a middle right coronary artery, a distal right coronary artery, and a posterior descending artery (PDA). That is, the type of coronary arteries may be classified as described above according to a location of the coronary artery. A myocardium image analysis device according to an embodiment of the present disclosure to be described below may classify the myocardium included in the myocardium image to a related region according to the type of coronary artery.

Figure 2:
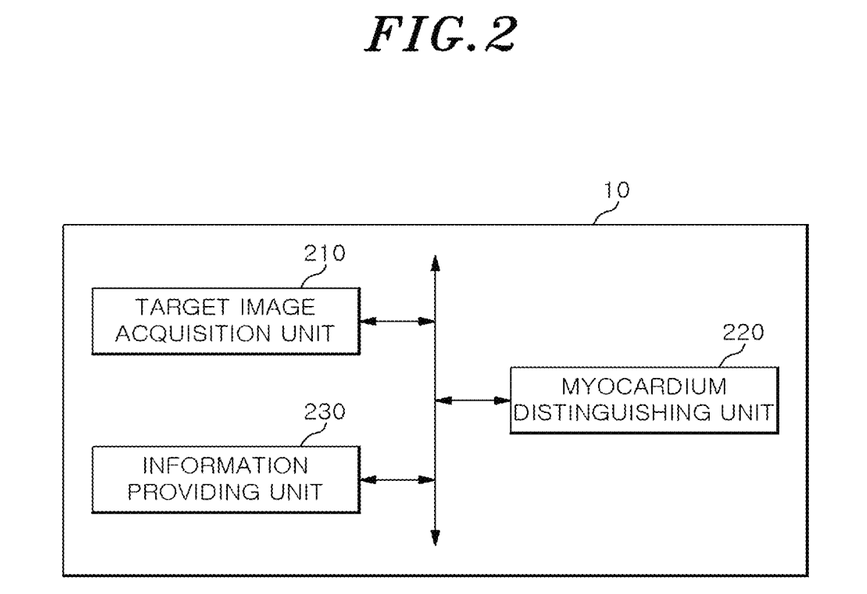
FIG. 2 illustrates an example of a functional configuration of a myocardium image analysis device according to an embodiment of the present disclosure.

FIG. 2 illustrates an example of a functional configuration of a myocardium image analysis device according to an embodiment of the present disclosure.

Referring to FIG. 2, a myocardium image analysis device 10 may include a target image acquisition unit 210, a myocardium distinguishing unit 220, and an information providing unit 230.

The target image acquisition unit 210 may acquire a target image for precontrast-enhanced myocardium. The target image may include a medical image. For example, the target image may include a computed tomography (CT) image, but is not limited thereto.

In some cases, it goes without saying that the target image may include organs other than the myocardium. However, since the target image is an image before a contrast medium is administered, the target image may be an image in an ambiguous state in which a boundary of each organ is not clearly revealed.

The myocardium distinguishing unit 220 may identify the coronary artery included in the target image by using the artificial neural network 102. Here, the artificial neural network 102 performs training based on a training database generated by matching the pre-acquired images of the pre-contrast-enhanced coronary artery and myocardium and the pre-acquired images of the postcontrast-enhanced coronary artery and myocardium. The training database may include information on at least one of a size, a location, a shape, and a length of a region of the myocardium related for each type of the coronary artery.

The pre-acquired images of the precontrast-enhanced coronary artery and myocardium and the pre-acquired images of the postcontrast-enhanced coronary artery and myocardium as an image of the same target, i.e., the same patient may be a vast amount of data stored in advance.

Meanwhile, there may be a plurality of images before and after the contrast enhancement used for the training of the artificial neural network 102, and the matched images before and after the contrast enhancement may be images of the same target. The matching of the images of the same target is easy for those skilled in the art, so a more detailed description related thereto may be omitted.

Meanwhile, the contrast medium may be administered to the patient and a medical image after the contrast enhancement may be acquired based thereon, and each organ in the medical image after the contrast enhancement is more clearly distinguished. The above-described artificial neural network 102 may be an algorithm that is learned to accurately distinguish each organ included in the image before the contrast enhancement when receiving the image before the contrast enhancement as an input image later by using the medical image after the contrast enhancement.

The region of the myocardium may be distinguished according to the type of coronary artery in the medical image after the contrast enhancement used for training the artificial neural network 102. As a result, in addition to distinguishing the myocardium region in the myocardium image, the artificial neural network 102 may be learned to distinguish the corresponding myocardium region in more detail according to the type of coronary artery.

The artificial neural network 102 may include a fully convolutional network (FCN). However, the artificial neural network 102 is not limited thereto, and may include various machine training algorithms (or a deep training algorithm or an artificial intelligence algorithm) related to image identification.

The myocardium distinguishing unit 220 may distinguish the myocardium in the target image by using the artificial neural network 102 and classify the related region of the distinguished myocardium in detail based on the type of coronary artery.

In more detail, the myocardium distinguishing unit 220 may distinguish the region of the myocardium according to the type of coronary artery which is positioned adjacent to the myocardium and exerts an influence on the myocardium. The distinguishing may be performed based on information on at least one of a size, a location, a shape, and a length of a region of the myocardium related for each type of the coronary artery.

The distinguished region of the myocardium may include, for example, a myocardium region connected to the left coronary artery, a myocardium region connected to the left main coronary artery, a myocardium region connected to the left anterior descending coronary artery, a myocardium region connected to the proximal left anterior descending artery, a myocardium region connected to the middle left anterior descending artery, a myocardium region connected to the distal left anterior descending artery, a myocardium region connected to the right coronary artery, a myocardium region connected to the proximal right coronary artery, a myocardium region connected to the middle right coronary artery, a myocardium region connected to the distal right coronary artery, and a myocardium region connected to the posterior descending artery.

The information providing unit 230 may provide information on the distinguished myocardium. The information providing unit 230 may provide information on the myocardium distinguished by the myocardium distinguishing unit 220. The information providing unit 230 may provide the information on the distinguished myocardium by various methods. The information providing unit 230 may provide the information on the myocardium by allowing the region of the myocardium distinguished by various methods including a color, a pattern, an effect, etc., to be revealed in the output image 103.

The information providing unit 230 may provide the information as the output image 103 by displaying the information on the distinguished myocardium to be revealed in the target image for the myocardium acquired as the input image 101. More specifically, the information providing unit 230 may provide the information as the output image 103 by displaying the myocardium to be distinguished from other organs in the input image 101 and allowing the related myocardium region to be revealed for each type of coronary artery.

In some cases, the information providing unit 230 may generate and provide an output image 103 in which the related myocardium region is displayed for each type of coronary artery based on the input image 101.

Figure 3:
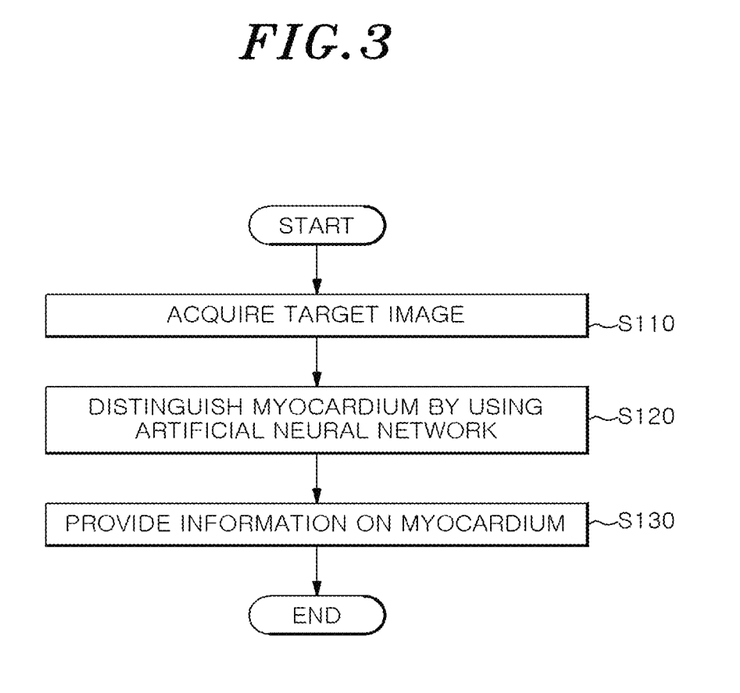
FIG. 3 illustrates a flow of each step of the myocardium image analysis method using an artificial neural network according to an embodiment of the present disclosure.

FIG. 3 illustrates a flow of each step of the myocardium image analysis method using an artificial neural network according to an embodiment of the present disclosure. Hereinafter, in FIG. 3, the myocardium image analysis method will be described based on each component of the myocardium image analysis device 10 of FIG. 2. Further, each step of the method illustrated in FIG. 3 may be performed in a different order illustrated in the figure in some cases, of course.

Referring to FIG. 3, the target image acquisition unit 210 may acquire a target image for precontrast-enhanced myocardium (S110). More specifically, the target image acquisition unit 210 may acquire, as the target image, a medical image including the coronary artery and the myocardium of a patient to which a contrast medium is not administered. The medical image may include various types of images medically used, and may include, for example, computed tomography (CT).

Meanwhile, the target image acquired by the target image acquisition unit 210 as a medical image before the contrast enhancement may be generally an image in which a distinction between the coronary artery and other organs is ambiguous.

The myocardium distinguishing unit 220 may distinguish the myocardium by using the artificial neural network 102 (S120). The myocardium distinguishing unit 220 may identify the myocardium in the target image by using the artificial neural network 102 and furthermore, distinguish the region of the myocardium included in the target image according to the type of coronary artery. The distinguished region of the myocardium may include, for example, a myocardium region connected to the left coronary artery, a myocardium region connected to the left main coronary artery, a myocardium region connected to the left anterior descending coronary artery, a myocardium region connected to the proximal left anterior descending artery, a myocardium region connected to the middle left anterior descending artery, a myocardium region connected to the distal left anterior descending artery, a myocardium region connected to the right coronary artery, a myocardium region connected to the proximal right coronary artery, a myocardium region connected to the middle right coronary artery, a myocardium region connected to the distal right coronary artery, and a myocardium region connected to the posterior descending artery.

The artificial neural network 102 may be an algorithm learned by using a training database acquired by matching the images of the precontrast-enhanced coronary artery and myocardium and images of the postcontrast-enhanced coronary artery and myocardium.

Here, the training database may include information on at least one of a size, a location, a shape, and a length of a region of the myocardium related for each type of the coronary artery. The images before and after the contrast enhancement used for the matching may be images for the same target, i.e., the same patient. The myocardium distinguishing unit 220 may identify the myocardium in the target image in detail based on the type of coronary artery by using the artificial neural network 102.

The information providing unit 230 may provide information on the distinguished myocardium (S130). In more detail, the information providing unit 230 may display the region of the myocardium to be revealed in the target image, and classify the region of the myocardium to related parts for each type of coronary artery and provide information thereon.

Figure 4:
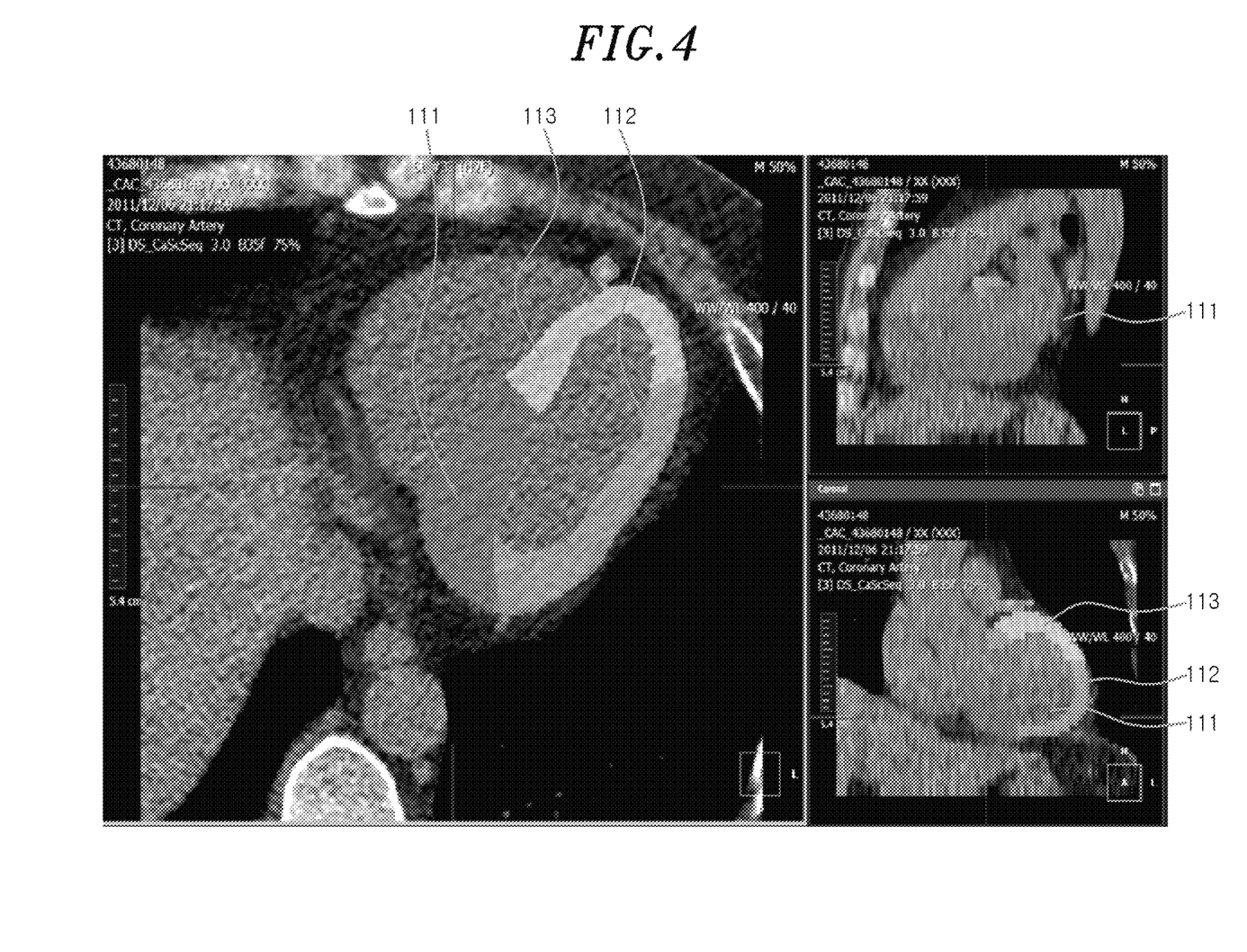
FIG. 4 illustrates an example of an output image of the myocardium image analysis device according to an embodiment of the present disclosure.

FIG. 4 illustrates an example of an output image of the myocardium image analysis device according to an embodiment of the present disclosure. The myocardium image analysis device 10 may perform an analysis by receiving an image for the myocardium, i.e., a myocardium image.

Referring to FIG. 4, the myocardium image analysis device 10 may provide an output image in which the myocardium is displayed to be clearly revealed in the myocardium image based on the artificial neural network 102.

FIG. 4 illustrates three examples of an output image, and it can be seen that a myocardium part is emphasized and revealed in each output image. As illustrated, in the myocardium region, a corresponding part may be displayed differently from other parts according to the type of related coronary artery in the output image. For example, information on the myocardium region distinguished by various methods such as displaying the color of the corresponding part differently, displaying the pattern differently, inputting and displaying a text, etc., may be provided in the form of the output image.

Since the region of the myocardium is automatically analyzed by the artificial neural network 102, the myocardium image analysis device 10 according to an embodiment of the present disclosure may provide objective and accurate information without intervention of a person, i.e., without depending on a subjective judgment of a doctor or an analyst.

Further, since the myocardium image analysis device 10 according to an embodiment of the present disclosure may identify a part for the myocardium and provide detailed and accurate information for the myocardium, with respect to a precontrast-enhanced heart image in which the myocardium is displayed to be ambiguous, the myocardium image analysis device 10 may acquire the information on the myocardium without contrast enhancement, thereby minimizing unnecessary contrast enhancement.

The combinations of the respective blocks of a block diagram and the combinations of the respective sequences of a flow diagram attached herein may be carried out by computer program instructions. Since the computer program instructions may be executed by the processor of a general purpose computer, a special purpose computer, or other programmable data processing apparatus, the instructions, executed by the processor of the computer or other programmable data processing apparatus, create means for performing functions described in the respective sequences of the flow diagram or the respective blocks of the block diagram. The computer program instructions, in order to implement functions in a specific manner, may be stored in a computer-readable storage medium or a computer-useable storage medium for other programmable data processing apparatus, and the instructions stored in the computer-readable storage medium or the computer-useable storage medium may produce manufacturing items that include means for instructions to perform the functions described in the respective sequences of the flow diagram or the respective blocks of the block diagram. The computer program instructions may be loaded in a computer or other programmable data processing apparatus, and therefore, the instructions, which are a series of sequences executed in a computer or other programmable data processing apparatus to create processes executed by a computer to operate a computer or other programmable data processing apparatus, may provide operations for executing functions described in the respective sequences of the flow diagram or the respective blocks of the block diagram.

Moreover, the respective block or the respective sequences may refer to two or more modules, segments, or codes including at least one executable instruction for executing a specific logic function(s). In some alternative embodiments, it is noted that the functions described in the sequences may be run out of order. For example, two consecutive sequences may be executed simultaneously or in reverse order according to the particular function.

The above description illustrates the technical idea of the present invention, and it will be understood by those skilled in the art to which this present invention belongs that various changes and modifications may be made without departing from the scope of the essential characteristics of the present invention. Therefore, the exemplary embodiments disclosed herein are not used to limit the technical idea of the present invention, but to explain the present invention, and the scope of the technical idea of the present invention is not limited by those embodiments. Therefore, the scope of protection of the present invention should be construed as defined in the following claims, and all technical ideas that fall within the technical idea of the present invention are intended to be embraced by the scope of the claims of the present invention.

What is claimed is:

1. A myocardium image analysis method comprising:
acquiring a target image including precontrast-enhanced myocardium;
based on a type of coronary artery related to the myocardium, dividing up the myocardium included in the target image, using an artificial neural network; and
providing information on the distinguished myocardium,
wherein the artificial neural network is trained based on a training database generated by matching images for training of precontrast-enhanced coronary artery and myocardium and pre-acquired images for training of postcontrast-enhanced coronary artery and myocardium.

2. The myocardium image analysis method of claim 1, wherein the type of coronary arteries includes a left coronary artery (LCA), a left main coronary artery (LMCA), a left anterior descending coronary artery (LAD), a proximal left anterior descending artery, a middle left anterior descending artery, a distal left anterior descending artery, a right coronary artery (RCA), a proximal right coronary artery, a middle right coronary artery, a distal right coronary artery, and a posterior descending artery (PDA).

3. The myocardium image analysis method of claim 1, wherein the dividing up of the myocardium includes dividing up the myocardium according to the type of coronary artery which is adjacent to the myocardium and exerts an influence on the myocardium.

4. The myocardium image analysis method of claim 1, wherein the training database includes information on at least one of a size, a location, a shape, and a length of a region of the myocardium related for each type of the coronary artery,
the artificial neural network includes a fully convolutional network (FCN), and
the region of the myocardium includes a myocardium region connected to the left coronary artery, a myocardium region connected to the left main coronary artery, a myocardium region connected to the left anterior descending coronary artery, a myocardium region connected to the proximal left anterior descending artery, a myocardium region connected to the middle left anterior descending artery, a myocardium region connected to the distal left anterior descending artery, a myocardium region connected to the right coronary artery, a myocardium region connected to the proximal right coronary artery, a myocardium region connected to the middle right coronary artery, a myocardium region connected to the distal right coronary artery, and a myocardium region connected to the posterior descending artery.

5. The myocardium image analysis method of claim 1, wherein the images for training of the precontrast-enhanced coronary artery and myocardium and the images for training of the postcontrast-enhanced coronary artery and myocardium are images on the same target.

6. The myocardium image analysis method of claim 1, wherein the target image is a computed tomography (CT) image.

7. A myocardium image analysis device comprising:
a target image acquisition unit acquiring a target image including precontrast-enhanced myocardium;
based on a type of coronary artery related to the myocardium, a myocardium distinguishing unit dividing up the myocardium included in the target image, using an artificial neural network; and
providing information on the distinguished myocardium,
wherein the artificial neural network is trained based on a training database generated by matching images for training of precontrast-enhanced coronary artery and myocardium and images for training of postcontrast-enhanced coronary artery and myocardium.

8. The myocardium image analysis device of claim 7, wherein the type of coronary arteries includes a left coronary artery (LCA), a left main coronary artery (LMCA), a left anterior descending coronary artery (LAD), a proximal left anterior descending artery, a middle left anterior descending artery, a distal left anterior descending artery, a right coronary artery (RCA), a proximal right coronary artery, a middle right coronary artery, a distal right coronary artery, and a posterior descending artery (PDA).

9. The myocardium image analysis device of claim 7, wherein the myocardium distinguishing unit divides the myocardium according to the type of coronary artery which is adjacent to the myocardium and exerts an influence on the myocardium.

10. The myocardium image analysis device of claim 7, wherein the training database includes information on at least one of a size, a location, a shape, and a length of a region of the myocardium related for each type of the coronary artery,
the artificial neural network includes a fully convolutional network (FCN), and
the distinguished region of the myocardium includes a myocardium region connected to the left coronary artery, a myocardium region connected to the left main coronary artery, a myocardium region connected to the left anterior descending coronary artery, a myocardium region connected to the proximal left anterior descending artery, a myocardium region connected to the middle left anterior descending artery, a myocardium region connected to the distal left anterior descending artery, a myocardium region connected to the right coronary artery, a myocardium region connected to the proximal right coronary artery, a myocardium region connected to the middle right coronary artery, a myocardium region connected to the distal right coronary artery, and a myocardium region connected to the posterior descending artery.

11. The myocardium image analysis device of claim 7, wherein the images for training of the precontrast-enhanced coronary artery and myocardium and the images for training of the postcontrast-enhanced coronary artery and myocardium are images for the same target.

12. The myocardium image analysis device of claim 7, wherein the target image is a computed tomography (CT) image.

13. A computer readable recording medium storing a computer program, comprising:
   acquiring a target image including precontrast-enhanced myocardium;
   based on a type of coronary artery related to the myocardium, dividing up the myocardium included in the target image, using an artificial neural network; and
   providing information on the distinguished myocardium,
   wherein the artificial neural network includes a command for allowing a processor to perform a myocardium image analysis method in which training is performed based on a training database generated by matching images for training of precontrast-enhanced coronary artery and myocardium and images for training of postcontrast-enhanced coronary artery and myocardium.

* * * * *